(12) United States Patent
Horowitz et al.

(10) Patent No.: US 12,377,244 B2
(45) Date of Patent: Aug. 5, 2025

(54) CATHETERS WITH EXPANDABLE AND COLLAPSIBLE LUMENS

(71) Applicant: Retriever Medical, Inc., Las Vegas, NV (US)

(72) Inventors: Michael Bruce Horowitz, Naples, FL (US); Brandon Matthew Repko, Mars, PA (US); Hieu Le, Fountain Valley, CA (US); Benjamin William Bobo, Las Vegas, NV (US)

(73) Assignee: Retriever Medical, Inc., Las Vegas, NV (US)

( * ) Notice: Subject to any disclaimer, the term of this patent is extended or adjusted under 35 U.S.C. 154(b) by 781 days.

(21) Appl. No.: 17/659,375

(22) Filed: Apr. 15, 2022

(65) Prior Publication Data

US 2022/0330959 A1 Oct. 20, 2022

Related U.S. Application Data

(60) Provisional application No. 63/175,527, filed on Apr. 15, 2021.

(51) Int. Cl.
*A61M 25/00* (2006.01)
*A61B 17/00* (2006.01)
*A61B 17/22* (2006.01)

(52) U.S. Cl.
CPC .... *A61M 25/0023* (2013.01); *A61M 25/0074* (2013.01); *A61B 2017/00867* (2013.01); *A61B 17/22* (2013.01); *A61B 2017/22038* (2013.01); *A61M 2025/0024* (2013.01); *A61M 2025/0025* (2013.01)

(58) Field of Classification Search
CPC .......... A61M 25/0023; A61M 25/0043; A61M 25/0074; A61M 2025/0024; A61M 2025/0025; A61M 2025/0035; A61M 2025/0058; A61M 2205/0283
See application file for complete search history.

(56) References Cited

U.S. PATENT DOCUMENTS

| | | | |
|---|---|---|---|
| 5,735,831 A | 4/1998 | Johnson et al. | |
| 2006/0217754 A1* | 9/2006 | Boehm, Jr. .......... | A61B 17/025 606/191 |
| 2009/0182278 A1 | 7/2009 | Eversull et al. | |
| 2011/0146689 A1* | 6/2011 | Curley ................. | A61M 16/04 128/207.14 |
| 2018/0263752 A1 | 9/2018 | Pinchuk et al. | |
| 2022/0062588 A1* | 3/2022 | Mintz ................... | A61B 17/22 |

* cited by examiner

*Primary Examiner* — Kami A Bosworth

(57) ABSTRACT

A catheter device that includes a conduit having an outer wall, an internal lumen, and proximal and distal ends. The conduit further includes first and second pluralities of electrical conduits embedded in the outer wall of the conduit, which are adapted to transmit electrical current therethrough in a first direction and an opposing second direction. The conduit is adapted to transition from a pre-collapsed state to a first collapsed state when the first plurality of electrical conduits transmits a first electrical current in a first direction and the second plurality of electrical conduits transmits a second electrical current in a second direction, and transition from the first collapsed state to a second expanded state when the first plurality of electrical conduits and the second plurality of electrical conduits transmit a third electrical current in the first direction.

5 Claims, 9 Drawing Sheets

300

305
A Catheter Device is Advanced into a Body Lumen and Positioned at a Target Location within the Body Lumen.

310
The Device is Made to Transition from a First Collapsed State to a Second Expanded State by Actuating an Electric Current to Flow in a First Direction Through each of a Plurality of Wires Embedded within a Wall of the Device.

315
The Device is Made to Transition from a Second Expanded State Back to the First Collapsed State by Actuating an Electric Current to Flow in a First Direction in a First Portion and in a Second Direction in a Second Portion of the Plurality of Wires

FIG. 3

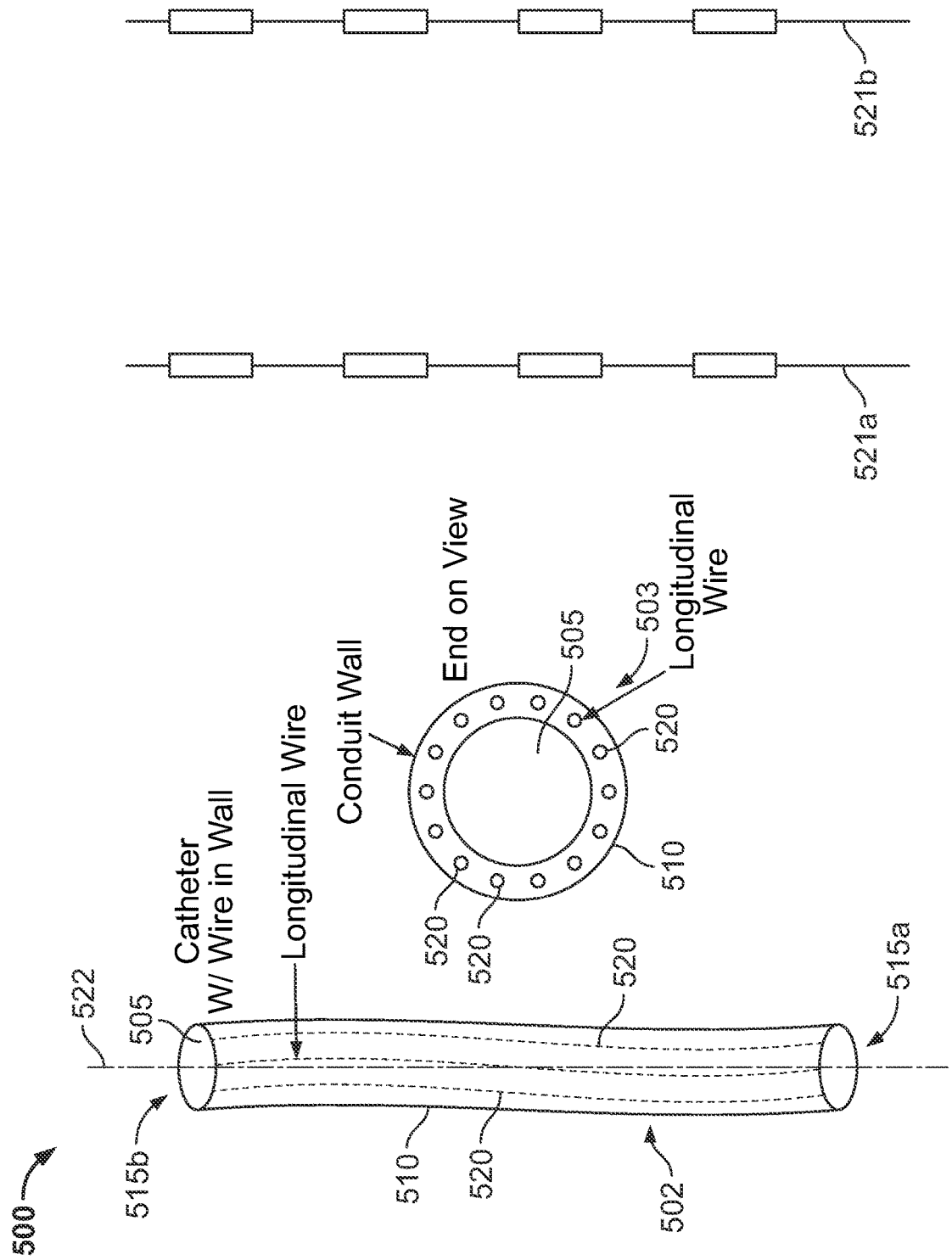

600

605

A Catheter Device is Advanced into a Body Lumen and Positioned at a Target Location within the Body Lumen. A Restraint Keeps the Device in a First Collapsed State.

610

The Device is Made to Transition from the First Collapsed State to a Second Expanded State by Removing the Restraint thereby Causing the Device to Assume the Second Expanded State.

615

The Device is Made to Transition from the Second Expanded State Back to the First Collapsed State by Introducing and Positioning a First Wire (having a Plurality of Magnets Attached thereto) within the Lumen.

FIG. 6

CATHETERS WITH EXPANDABLE AND COLLAPSIBLE LUMENS

CROSS REFERENCE

The present application relies on U.S. Patent Provisional Application No. 63/175,527 ('527 application), entitled "Catheters with Expandable and Collapsible Lumens" and filed on Apr. 15, 2021 for priority. The '527 application is herein incorporated by reference.

FIELD

The present specification is related generally to the field of catheters. More specifically the present specification is related to low profile catheters that, after insertion into the vessel of an animal, can be transitioned from a collapsed first state to an expanded second state and vice versa.

BACKGROUND

Catheter devices enable delivering a variety of different therapies, tools, implantables, or other devices into various parts of human or animal bodies. Medical devices such as dilation balloons, occlusion balloons, thrombectomy treatment devices, stents, and embolic filters, and therapeutic agents such as drugs and radiation sources, may be positioned at or near a distal end of a catheter for delivery to a desired site within the body.

Frequently, to deliver the right procedural tools to a particular anatomical site, a catheter with a large lumen diameter is required. However, percutaneously delivering a large lumen catheter through tortuous arterial and/or venous pathways, and within spaces of various anatomy structures, is extremely difficult, if not impossible. Owing to the catheter's large lumen, it can be arduous and sometimes traumatic to maneuver and position the catheter at certain target locations within the body. While, in theory, one can decrease the catheter lumen to enable for an easier delivery, a narrow catheter lumen would make eliminate the ability to deliver the requisite tools, implantables, or other devices to the desired anatomical site via an excessively narrow lumen.

Accordingly, there is thus a need for a catheter that may be configured to have a small lumen diameter during the process of introducing and advancing the catheter within a body lumen and may be configured to transition to a larger lumen once positioned at a target location within the body lumen. There is also need for the catheter to be able to readily transition from the small lumen to the large lumen and vice versa depending upon clinical needs and goals.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a catheter device, comprising: a wall enclosing a lumen extending therethrough, wherein the lumen has a proximal end and a distal end; an occluded aperture at the distal end of the lumen; and an indeflator coupled to the proximal end of the lumen and configured to inject a fluid into the lumen, wherein, when the injected fluid is injected to lumen and increases pressure within the lumen, the wall expands from a first state to a second state and, when a pressure in the lumen from the injected fluid reaches or exceeds a threshold pressure, the occluded aperture is configured to open to permit the fluid to flow out of the lumen.

Optionally, the catheter device further comprises a wire positioned within the lumen and configured to be removable from the lumen.

Optionally, the aperture is occluded by a membrane or a forced restriction that blocks the aperture.

Optionally, the fluid is air, saline or water.

Optionally, the first state corresponds to a collapsed configuration and the second state corresponds to an expanded configuration of the device. Optionally, in the first state, the wall has a first surface area, encloses a first volume, and has a first circumference and, in the second state, the wall has a second surface area, equal to the first surface area, a second circumference that is greater than the first circumference, and a second volume that is greater than the first volume.

Optionally, in the first state, an internal diameter of the lumen is less than 6 French and, in the second state, the internal diameter of the lumen is greater than 16 French.

Optionally, in the first state, an internal diameter of the lumen is less than 4 French and, in the second state, the internal diameter of the lumen is greater than 18 French.

Optionally, in the first state, an outer diameter of the lumen is less than 8 French and, in the second state, the outer diameter of the lumen is greater than 18 French.

Optionally, in the first state, a volume of the lumen is less than 1 cm$^3$ and, in the second state, the volume of the lumen is greater than 2,500 cm$^3$.

The present specification also discloses a method of transitioning a catheter from a collapsed state to an expanded state, the device having a wall enclosing a lumen extending therethrough wherein the lumen has a proximal end and a distal end, an occluded aperture at the distal end of the lumen, and an indeflator coupled to a proximal end of the lumen and configured to inject a fluid into the lumen, the method comprising: positioning the catheter at a target location in a body lumen, wherein the catheter is in a collapsed in the first state; using the indeflator, injecting the fluid into the proximal end of the lumen, wherein, when the injected fluid is injected to lumen and increases pressure within the lumen, the wall expands from the collapsed state to the expanded state and, when a pressure in the lumen from the injected fluid reaches or exceeds a threshold pressure, the occluded aperture ruptures or opens to permit the fluid to flow out of the lumen with the wall remaining in the expanded state.

Optionally, the catheter further comprises a wire positioned within the lumen. Optionally, the method further comprises withdrawing the wire from the lumen through the proximal end.

Optionally, the aperture is occluded by a membrane or a forced restriction that blocks the aperture.

Optionally, the fluid is air, saline or water.

Optionally, in the collapsed state, the wall has a first surface area, encloses a first volume, and has a first circumference and, in the expanded state, the wall has a second surface area, equal to the first surface area, a second circumference that is greater than the first circumference, and a second volume that is greater than the first volume.

Optionally, in the collapsed state, an internal diameter of the lumen is less than 6 French and, in the expanded state, the internal diameter of the lumen is greater than 16 French.

Optionally, in the collapsed state, an internal diameter of the lumen is less than 4 French and, in the expanded state, the internal diameter of the lumen is greater than 18 French.

Optionally, in the collapsed state, an outer diameter of the lumen is less than 8 French and, in the expanded state, the outer diameter of the lumen is greater than 18 French.

Optionally, in the collapsed state, a volume of the lumen is less than 1 cm$^3$ and, in the expanded state, the volume of the lumen is greater than 2,500 cm$^3$.

The present specification also discloses a catheter device configured to transition between a first state having a first lumen circumference to a second state having a second lumen circumference, wherein the first lumen circumference is less than the second lumen circumference, comprising: a wall enclosing a lumen extending therethrough, wherein the lumen defines a longitudinal axis substantially parallel to the wall; a plurality of wires embedded within the wall, wherein each of the plurality of wires is oriented substantially parallel to a longitudinal axis of the device; and a controller in electrical communication with the plurality of wires, wherein the controller is configured to cause electric current to flow through the plurality of wires, wherein the device is configured to assume the second state when the electric current through the plurality of wires is reversed, wherein the controller is further configured to cause electric current to flow through a first portion of the plurality of wires in a first direction and concurrently cause electric current to flow through a second portion of the plurality of wires in a second direction, and wherein the device is configured to assume the first state when the electric current flows through the first portion of the plurality of wires in the first direction and concurrently flows through the second portion of the plurality of wires in the second direction.

Optionally, the plurality of wires extends along an entire length of the device.

Optionally, the plurality of wires extends along a portion of the device.

Optionally, the plurality of wires is positioned substantially longitudinally about the longitudinal axis.

Optionally, the plurality of wires is configured to generate a mutually repelling magnetic force when electric current flows through the plurality of wires in the first direction.

Optionally, the plurality of wires is configured such that an attractive magnetic force sufficient to collapse the lumen is generated between the first and the second portions of the plurality of wires when electric current flows through the first portion of the plurality of wires in the first direction and through the second portion of the plurality of wires in the second direction.

Optionally, the first state corresponds to a collapsed configuration of the lumen and the second state corresponds to an expanded configuration of the lumen.

The present specification also discloses a method of transitioning a catheter device from a first state to a second state, wherein the catheter device has a wall enclosing a lumen and a plurality of wires embedded within the wall, the method comprising: enabling electric current to flow through the plurality of wires in a first direction, wherein the device assumes the second state when the electric current flows through all of the plurality of wires in the first direction; and enabling electric current to flow through a first portion of the plurality of wires in the first direction and concurrently through a second portion of the plurality of wires in a second direction opposite to the first direction to thereby cause the device to transition from the second state to the first state.

Optionally, each of the plurality of wires is oriented substantially parallel to a longitudinal axis of the device.

Optionally, the plurality of wires extends along an entire length of the device.

Optionally, the plurality of wires extends along a portion of the device.

Optionally, the plurality of wires is positioned substantially longitudinally about the longitudinal axis.

Optionally, the plurality of wires generates a mutually repelling magnetic force when electric current flows through the plurality of wires in the first direction.

Optionally, an attractive magnetic force is generated between the first and second portions of the plurality of wires when electric current flows through the first portion in the first direction and through the second portion in the second direction.

Optionally, the first state corresponds to a collapsed configuration of the lumen and the second state corresponds to an expanded configuration of the lumen.

The present specification also discloses a catheter device configured to transition between a collapsed state and an expanded state, comprising: a wall enclosing a lumen; a first wire embedded within the wall, wherein the first wire forms a circumferential helical wind about a longitudinal axis of the device; a second wire adapted to be removably positioned within the lumen; and a controller configured to generate and transmit an electrical current to the first wire and/or the second wire, wherein when the controller is activated to flow an electric current through the first wire and the second wire in a first direction the lumen adopts the expanded state, and wherein when the controller is activated to reverse a direction of flow of the electric current through either the first wire or the second wire, the lumen transitions from the expanded state to the collapsed state.

Optionally, the second wire is oriented substantially parallel to the longitudinal axis when positioned within the lumen.

Optionally, the first wire extends along an entire length of the device.

Optionally, the first wire extends along a portion of the device.

Optionally, the first wire and the second wire are configured to generate a mutually repelling magnetic force sufficient to expand the lumen when electric current flows through them in the first direction.

Optionally, the first wire and the second wire are configured to generate an attractive magnetic force sufficient to collapse the lumen when electric current flows in opposite directions in the first wire and the second wire.

Optionally, the lumen is configured to be able to repeatedly adopt either the first state or the second state.

The present specification also discloses a method of transitioning a catheter device from a first state to a second state, the device having a wall enclosing a lumen, a first wire embedded within the wall and a second wire removably positioned within the lumen, wherein the first wire forms a circumferential helical wind about a longitudinal axis of the device, the method comprising: enabling electric current to flow through the first and second wires in a first direction, wherein the device assumes the second state when the electric current flows through the first and second wires in the first direction; and enabling electric current to flow through either the first wire or the second wire in a second direction opposite to the first direction, wherein the device transitions from the second state to the first state when the electric current flows through the first and second wires in opposite directions.

Optionally, the second wire is oriented substantially parallel to the longitudinal axis when positioned within the lumen.

Optionally, the first wire extends along an entire length of the device.

Optionally, the first wire extends along a portion of the device.

Optionally, the first and second wires generate a mutually repelling magnetic force when electric current flows through them in the first direction.

Optionally, an attractive magnetic force is generated between the first and second wires when electric current flows in opposite directions in the first and second wires.

Optionally, the first state corresponds to a collapsed configuration and the second state corresponds to an expanded configuration of the device.

The present specification also discloses a catheter device being capable of transitioning from a first state to a second state, comprising: a wall enclosing a lumen; a plurality of stacks of first magnets embedded within the wall, wherein each of the plurality of stacks is oriented substantially parallel to a longitudinal axis of the device, wherein each magnet of the plurality of stacks has a first polarity, and wherein the device is kept in the first state using a restraint to restrain the wall; a first wire having a plurality of second magnets coupled to the first wire, and wherein each of the plurality of second magnets has a second polarity opposite to the first polarity; and a second wire having a plurality of third magnets coupled to the second wire, wherein each of the plurality of third magnets has the first polarity, wherein when the restraint is removed the device assumes the second state, and wherein when the first wire is positioned within the lumen the device transitions from the second state to the first state.

Optionally, when the device is in the second state, the second wire is positioned within the lumen to force the lumen to open further.

Optionally, the plurality of stacks extends along an entire length of the device.

Optionally, the plurality of stacks extends along a portion of a length of the device.

Optionally, the first magnets of the plurality of stacks and the third magnets of the second wire generate a mutually repelling magnetic force when the second wire is positioned within the lumen.

Optionally, an attractive magnetic force is generated between the first magnets of the plurality of stacks and the second magnets of the first wire when the first wire is positioned within the lumen.

Optionally, the first state corresponds to a collapsed configuration and the second state corresponds to an expanded configuration of the device.

The present specification also discloses a method of transitioning a catheter device from a first state to a second state, the device having a wall enclosing a lumen, a plurality of stacks of first magnets embedded within the wall, a first wire having a plurality of second magnets coupled to the first wire, a second wire having a plurality of third magnets coupled to the second wire, wherein the first and third magnets have a first polarity and the second magnets have a second polarity opposite to the first polarity, and wherein the device is kept in the first state using a restraint to restrain the wall, the method comprising: removing the restraint to enable the device to assume the second state; and positioning the first wire within the lumen to transition the device from the second state to the first state.

Optionally, when the device is in the second state, the second wire is positioned within the lumen to force the lumen open further.

Optionally, the plurality of stacks extends along an entire length of the device.

Optionally, the plurality of stacks extends along a portion of a length of the device.

Optionally, the first magnets of the plurality of stacks and the third magnets of the second wire generate a mutually repelling magnetic force when the second wire is positioned within the lumen.

Optionally, an attractive magnetic force is generated between the first magnets of the plurality of stacks and the second magnets of the first wire when the first wire is positioned within the lumen.

Optionally, the first state corresponds to a collapsed configuration and the second state corresponds to an expanded configuration of the device.

The present specification also discloses a catheter device being capable of transitioning from a first state to a second state, said device having proximal and distal ends and comprising: a wall enclosing a lumen; a wire positioned within the lumen when said device is in the first state; an occluded aperture at the distal end when said device is in the first state; and an indeflator coupled to the proximal end and configured to inject a fluid into the lumen, wherein the wire is removed from the lumen prior to injecting the fluid, and wherein due to the injected fluid when a pressure within the lumen reaches or exceeds a threshold the aperture at the distal end opens causing the device to transition from the first state to a second state.

Optionally, the aperture is occluded by a membrane or a forced restriction that blocks the aperture.

Optionally, the first state corresponds to a collapsed configuration and the second state corresponds to an expanded configuration of the device.

The present specification also discloses a method of transitioning a catheter device from a first state to a second state, the device having a wall enclosing a lumen, a wire positioned within the lumen when the device is in the first state, an occluded aperture at a distal end of the device when the device is in the first state, and an indeflator coupled to a proximal end of the device, the method comprising: positioning the device at a target location in a body lumen, said device being in the first state; withdrawing the wire from the lumen through the proximal end; and using the indeflator to inject a fluid into the lumen, wherein when a pressure due to the injected fluid within the lumen reaches or exceeds a threshold the aperture at the distal end opens causing the device to transition from the first state to a second state.

Optionally, the aperture is occluded by a membrane or a forced restriction that blocks the aperture.

Optionally, the first state corresponds to a collapsed configuration and the second state corresponds to an expanded configuration of the device.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 3 is a flowchart of a plurality of steps of a method of using the device of FIG. 1A, in accordance with some embodiments of the present specification;

FIG. 5 illustrates first and second views of another catheter or conduit device that is electrically or magnetically expandable and collapsible, in accordance with some embodiments of the present specification;

FIG. 6 is a flowchart of a plurality of steps of a method of using the device of FIG. 5, in accordance with some embodiments of the present specification;

DETAILED DESCRIPTION

Figure 1:
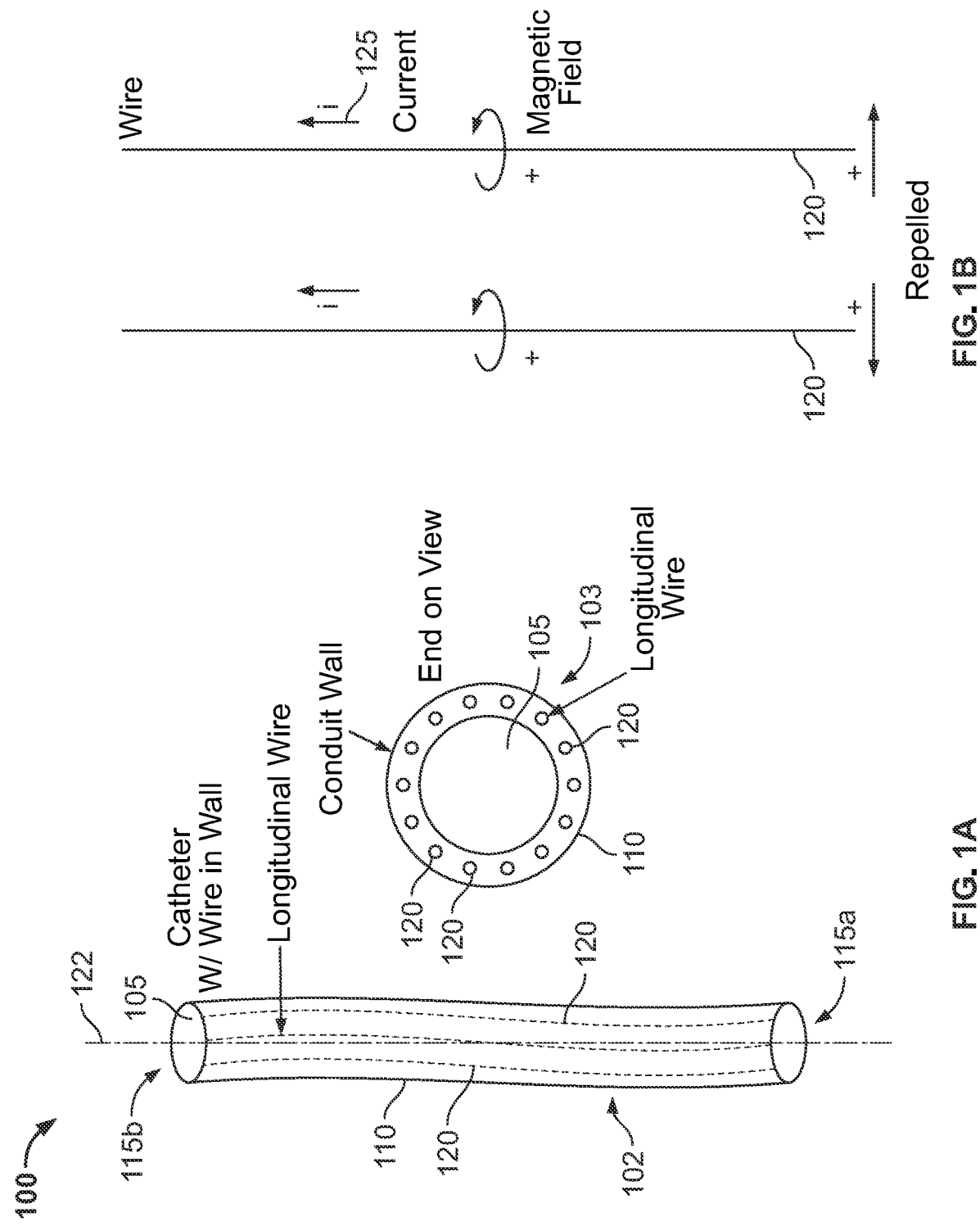
FIG. 1A illustrates first and second views of a catheter or conduit device that is electrically or magnetically expandable and collapsible, in accordance with some embodiments of the present specification.
FIG. 1B illustrates direction of flow of electric current through a plurality of wires embedded within a wall of the device of FIG. 1A, in accordance with some embodiments of the present specification.

The present specification is directed towards magnetically manipulatable catheter devices each of which has a wall enclosing a lumen. In one embodiment, a plurality of wires is embedded within the wall, wherein direction of flow of electrical current through the plurality of wires is modulated to enable the catheter device to be in a first collapsed state or second expanded state.

In another embodiment, a first wire is embedded within the wall and is helically wound along a length of the catheter device. A second wire is provided that is removably positioned within the lumen. The direction of flow of electric current through the first and second wires is modulated to enable the catheter device to be in a first or second state.

In a third embodiment, a plurality of stacks of first magnets is embedded within the wall. Restraints, such as a shackle, cage, mesh, or other structure, restrains and keeps the catheter device in the first collapsed state. A first wire is provided having a plurality of second magnets coupled thereto. A second wire is also provided having a plurality of third magnets coupled thereto. The first and second wires are configured to be removably positioned within the lumen.

The present specification is directed towards multiple embodiments of magnetically manipulatable catheter devices. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention.

Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

First Embodiment

FIG. 1A illustrates first and second views 102, 103 of a catheter or conduit device 100 that is electrically or magnetically expandable and collapsible, in accordance with some embodiments of the present specification. As shown in the first view 102, the device 100 has a circumferential wall 110 that defines, encloses or surrounds (over an angular span of 360 degrees) a lumen 105 therewithin. The device 100 has proximal and distal ends 115a, 115b that are open and unobstructed.

In embodiments, the conduit wall 110 is redundant (using foldable material and/or thin collapsible foils) such that the wall 110 can be transitioned from a first state to a second state and vice versa, as desired. The first state corresponds to a collapsed or contracted state of the wall 110 while the second state corresponds to an expanded or dilated state of the wall 110. In particular, when in a collapsed state, the conduit wall 110 comprises excess material such that it has a folded, rumpled, crimped, or crumbled configuration defining a first surface area and, when in an expanded state, the conduit wall 110 comprises a stretched or taut surface area having a second surface area, where the first and second surface areas are equal, even though the lumen of the conduit in the second state is greater than the lumen in the collapsed first state.

As shown in the transverse cross-sectional view 103, in some embodiments, a plurality of wires 120 are embedded within the wall 110 such that each of the plurality of wires 120 is oriented substantially parallel to a longitudinal axis 122 of the device 100.

In some embodiments, the plurality of wires 120 is positioned substantially longitudinally about the longitudinal axis 122 so that they cover an angular span of at least 0 degrees and up to 360 degrees around the lumen 105.

In embodiments, the plurality of wires 120 extends along at least a portion of the device 100 substantially parallel to the longitudinal axis 122. In some embodiments, the plurality of wires 120 extends along an entire length (from the proximal end 115a to the distal end 115b) of the device 100.

In some embodiments, the plurality of wires 120 extends only along a portion of the device 100.

As shown in FIG. 1B, the plurality of wires 120 forms a circuit such that, when desired, electric current 125 can be made to flow through at least some of the plurality of wires 120 in a first direction and, when desired, through at least some of the plurality of wires 120 in a second direction opposite to the first direction. It should be appreciated that due to flowing current, each of the plurality of wires 120 functions as an electromagnet or solenoid. Thus, when electric current 125 flows in the first direction, a circumferential magnetic field is generated by each of the plurality of wires 120 having a first polarity. When electric current 125 flows in the second direction a circumferential magnetic field is generated by each of the plurality of wires 120 having a second polarity opposite to the first polarity.

It should further be appreciated that the electrical current may be controlled through an actuator integrated into a housing or handle attached, coupled, or in electrical communication with the catheter. The actuator may be a button, switch, slider, or other interface that, when manipulated, causes a controller, which may comprise at least one processor executing a plurality of programmatic instructions stored in a memory, to generate and transmit the electrical current or terminate the electrical current.

To ease introduction and positioning of the device 100 within a blood vessel or anatomical structure, the device 100 should be in the first state—that is, collapsed or contracted. To enable the device 100 to be in the first state, electric current 125 is made to flow through a first portion of the plurality of wires 120 in a first direction and through a second portion of the plurality of wires 120 in a second direction (opposite to the first direction). This causes the first portion of wires to develop a first polarity and the second portion of wires to develop a second polarity (opposite to the first polarity). Consequently, the first portion of wires attracts the second portion of wires causing the wall 110 to be pulled inwards towards the lumen 105 thereby putting the device 100 in the first state.

In some embodiments, the first portion of wires range from 10% to 80% of the plurality of wires 120. In some embodiments, the first portion of wires is 50% of the plurality of wires 120.

It should be appreciated, that in some embodiments the device 100 may already be in the first state, by default, for ease of introduction and positioning of the device 100 within the blood vessel or anatomical structure.

Once the device 100 is positioned at a target location within the blood vessel or anatomical structure, electric current 125 is made to flow in a first direction through each of the plurality of wires 120, which causes each of the plurality of wires 120 to develop a same first polarity. Consequently, the plurality of wires 120 repel each other and in doing so cause the conduit wall 110 to be in the second state—that is, expand or dilate. Thus, the repelling plurality of wires 120 forces the conduit open so that it takes the shape of an elongated tube, catheter or conduit. As the wall 110 expands the inner diameter of the lumen 105 and the outer diameter of the device 100 increases. Thus, the catheter lumen volume, as well as the inner and outer surface areas of the device 100, increases. When the current 125 is unidirectional the device 100 will remain patent and if the magnetic fields are of sufficient strength, the repelling forces of the device 100 will withstand collapse even if negative pressure (aspiration) is applied to the lumen 105.

The device 100 can either expand fully or partially depending upon the amount of current applied which adjusts the strength of the magnetic fields and the resultant opposing forces.

To ease removal of the device 100 from the target position and/or to trap material (thrombus or clot material, for example) within the lumen 105 there may be a need to forcibly place the device 100 in the first state (collapsed or contracted).

To achieve the first state, the direction of flow of electric current is reversed to be in a second direction (opposite to the first direction) in a first portion of the plurality of wires 120 while the direction of flow of electric current continues to remain in the first direction in the remaining second portion of the plurality of wires 120. This reversal creates opposite attractive magnetic forces that collapses or contracts the device 100 thereby putting it in the first state.

In various embodiments, the entire length of the device 100 or only portions thereof can be expanded/dilated or collapsed/contracted depending upon clinical needs and goals.

In various embodiments, the device 100 of the present specification has a longitudinal length ranging from a first length 45 cm to a second length 150 cm (or any set of numerical increments therein, such as 45 cm to 50 cm or 60 cm to 130 cm), an internal diameter of the lumen 105 ranging from a first diameter 2 F (0.67 mm) when collapsed to a second diameter 22 F (7.3 mm) when fully expanded (or any set of numerical increments therein, such as 3 F to 7 F or 5 F to 20 F), an outer diameter of the device 100 ranging from a third diameter 4 F (1.3 mm) to a fourth diameter 24 F (8 mm) when fully expanded (or any set of numerical increments therein, such as 5 F to 8 F or 7 F to 24 F), a thickness of the wall 110 ranging from a first thickness 0.33 mm to a second thickness 1 mm (or any set of numerical increments therein, such as 0.4 mm to 0.8 mm or 0.5 mm to 1 mm), a volume of the device 100 ranging from a first volume 0.0035 $cm^3$ to a second volume 5,194.2 $cm^3$ (or any set of numerical increments therein, such as 0.05 $cm^3$ to 4000 $cm^3$ or 1 $cm^3$ to 5000 $cm^3$), and an outer surface area of the device 100 ranging from a first area 94.7 $cm^2$ to a second area 3,440 $cm^2$ (or any set of numerical increments therein, such as 100 $cm^2$ to 3000 $cm^2$ or 144 $cm^2$ to 3400 $cm^2$).

In some embodiments, in the first state, the wall 110 has a first surface area, encloses a first volume, and has a first circumference and, in the second state, the wall 110 has a second surface area, equal to the first surface area, a second circumference that is greater than the first circumference, and a second volume that is greater than the first volume.

In some embodiments, the device 100 of the present specification has a longitudinal length ranging from less than 50 cm to greater than 100 cm.

In some embodiments, the length ranges from less than 60 cm to greater than 140 cm.

In some embodiments, the device 100 of the present specification has an internal diameter of the lumen 105 ranging from less than 6 F when collapsed to greater than 16 F when fully expanded. In some embodiments, an internal diameter of the lumen 105 ranges from less than 4 F when collapsed to greater than 18 F when fully expanded. In some embodiments, an internal diameter of the lumen 105 ranges from less than 4 F when collapsed to greater than 6 F when fully expanded. In some embodiments, an internal diameter of the lumen 105 ranges from less than 3 F when collapsed to greater than 20 F when fully expanded.

In some embodiments, the device 100 of the present specification has an outer diameter of the lumen 105 ranging from less than 8 F when collapsed to greater than 18 F when fully expanded. In some embodiments, an outer diameter of the lumen 105 ranges from less than 10 F when collapsed to greater than 17 F when fully expanded. In some embodiments, an outer diameter of the lumen 105 ranges from less than 5 F when collapsed to greater than 22 F when fully expanded.

In some embodiments, the device 100 of the present specification has a thickness of the wall 110 ranging from less than 0.4 mm to greater than 0.9 mm. In some embodiments, a thickness of the wall 110 ranges from less than 0.35 mm to greater than 0.75 mm.

In some embodiments, the device 100 of the present specification has a volume of the lumen 105 ranging from less than 1 $cm^3$ when collapsed to greater than 2,500 $cm^3$ when fully expanded. In some embodiments, a volume of the lumen 105 ranges from less than 0.5 $cm^3$ when collapsed to greater than 3,500 $cm^3$ when fully expanded. In some embodiments, a volume of the lumen 105 ranges from less than 0.1 $cm^3$ when collapsed to greater than 5,000 $cm^3$ when fully expanded. In some embodiments, a volume of the lumen 105 ranges from less than 0.005 $cm^3$ when collapsed to greater than 4,000 $cm^3$ when fully expanded.

In some embodiments, the device 100 of the present specification has an outer surface area ranging from less than 100 $cm^2$ to greater than 3,000 $cm^2$. In some embodiments, an outer surface area of the device 100 ranges from less than 300 $cm^2$ to greater than 2,000 $cm^2$.

In various embodiments, the wall of the device 100 is fabricated using materials such as medical grade thermoplastics, but not limited to polyurethane, PEBAX and nylon.

FIG. 3 is a flowchart of a plurality of steps of a method 300 of using the device 100 of FIG. 1A, in accordance with some embodiments of the present specification. In a non-limiting exemplary use case, the method 300 is implemented to use the device 100 to access a body lumen such as, for example, a lumen of a blood vessel or an anatomical structure for performing a mechanical aspiration thrombectomy.

At step 305, the device 100 is advanced into a body lumen and positioned at a target location within the body lumen. In some embodiments, the device 100 is in a first state (that is, collapsed or contracted) during advancement and positioning at the target location.

In some embodiments, to enable positioning of the device 100 within the body lumen, a delivery catheter (having a detachable proximal hub, in some embodiments) is first advanced to the target location.

Next, the proximal hub of the delivery catheter is removed and the device 100 is advanced (from a proximal end of the delivery catheter) through the delivery catheter to the target location.

In some embodiments, the device 100 has a detachable proximal hub and more proximally situated integrated aspiration and introducer side port. Thereafter, the proximal hub of the device 100 and the delivery catheter are removed thereby leaving the device 100 positioned at the target location.

At step 310, the device 100 is made to transition from the first state to a second state of being expanded or dilated. To enable this state transition, electric current is made to flow in a first direction through each of a plurality of wires embedded within a wall of the device 100 using the aforementioned actuator and controller, which causes each of the plurality of wires to develop a same first polarity. Consequently, the plurality of wires repel each other and in doing so cause the wall to be in the second state—that is, expand or dilate. Thus, the repelling plurality of wires forces the device 100 open so that it takes the shape of an elongated tube, catheter or conduit.

Sustained application of the electric current holds the device 100 in an open position—that is, the second state. The device 100 can either expand fully or partially depending upon the amount of current applied which adjusts the strength of the magnetic fields and the resultant opposing forces.

At step 315, the device 100 is made to transition from the second state back to the first state. The transition from the second state back to the first state may be needed to ease removal of the device 100 from the target position and/or to trap material (thrombus or clot material, for example) within a lumen of the device 100. To enable this state transition, the direction of flow of electric current is reversed to be in a second direction (opposite to the first direction) in a first portion of the plurality of wires while the direction of flow of electric current continues to remain in the first direction in the remaining second portion of the plurality of wires. This reversal creates opposite attractive magnetic forces that in turn collapses or contracts the device 100 thereby putting it back in the first state.

It should be appreciated, that step 305 assumes that the device 100 is in the first state by default.

In some embodiments, where the device 200 is not in the first state by default, the device 100 may need to be forced into the first state by ensuring that electric current flows in a first direction through a first portion of the plurality of wires and flows in a second direction through a remaining second portion of the plurality of wires in order to create opposite polar charges in the first and second portions causing them to be pulled towards each other (as also described in step 315).

Second Embodiment

Figure 2:
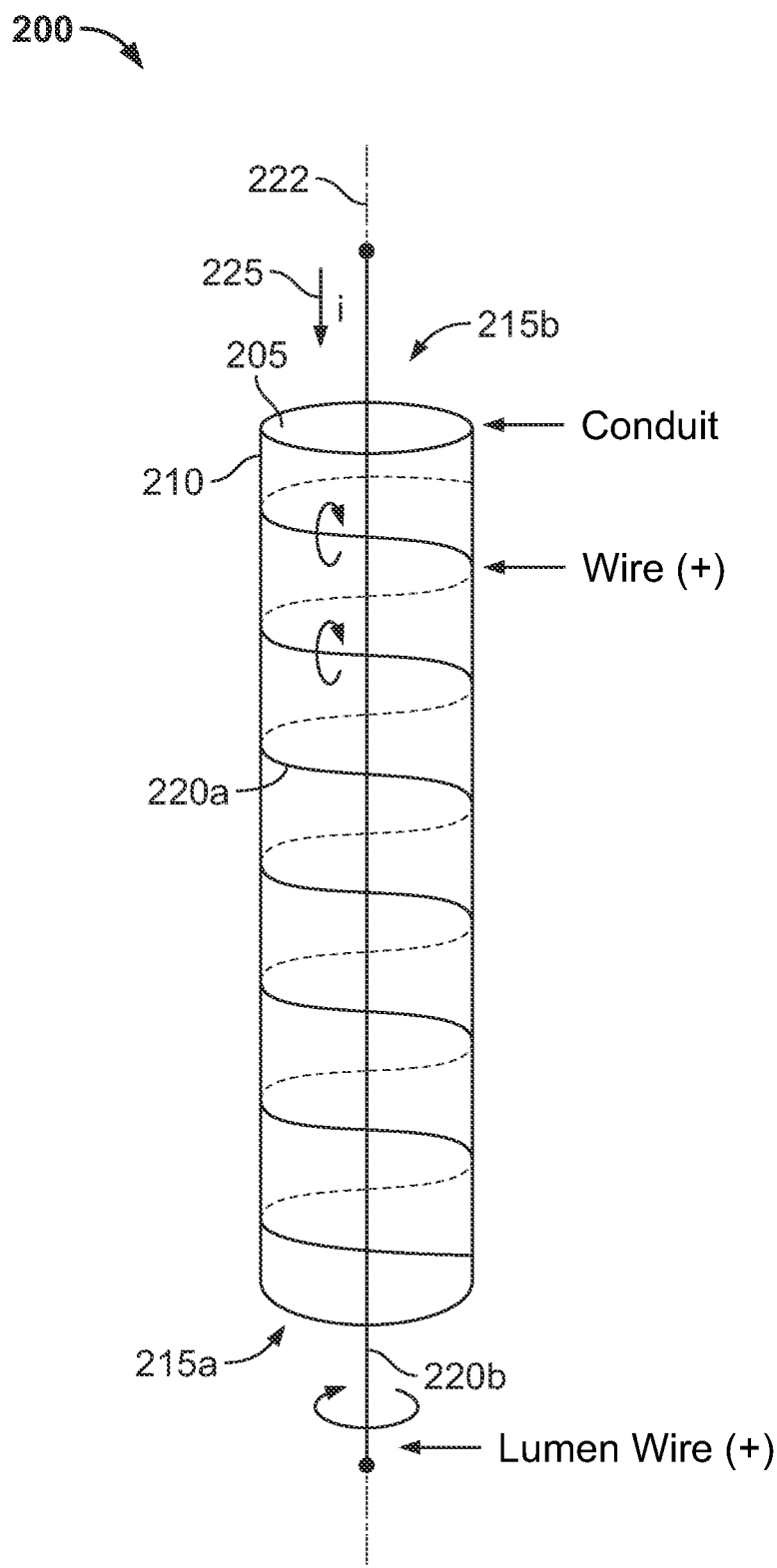
FIG. 2 illustrates another catheter or conduit device that is electrically or magnetically expandable and collapsible, in accordance with some embodiments of the present specification.

FIG. 2 illustrates a catheter or conduit device 200 that is electrically or magnetically expandable and collapsible, in accordance with some embodiments of the present specification.

As shown, the device 200 has a circumferential wall 210 that encloses or surrounds (over an angular span of 360 degrees) a lumen 205 therewithin. The device 200 also has proximal and distal ends 215a, 215b that are open and unobstructed.

In embodiments, the conduit wall 210 is redundant (using foldable material and/or thin collapsible foils) such that the wall 210 can be transitioned from a first state to a second state and vice versa, as desired. In particular, when in a collapsed state, the conduit wall 210 comprises excess material such that it has a folded, rumpled, crimped, or crumbled configuration defining a first surface area and, when in an expanded state, the conduit wall 210 comprises a stretched or taut surface area having a second surface area, where the first and second surface areas are equal, even though the lumen of the conduit in the second state is greater than the lumen in the collapsed first state. The first state corresponds to a collapsed or contracted state of the wall 210 while the second state corresponds to an expanded or dilated state of the wall 210.

As shown, embedded in the conduit wall 210 is a first wire 220a that has a circumferential helical wind about a longitudinal axis 222 (or the lumen 205).

In embodiments, the helical wind of the first wire 220a extends along at least a portion of a length of the device 200 substantially parallel to the longitudinal axis 222. In some embodiments, the helical wind of the first wire 220a extends along an entire length (from the proximal end 215a to the distal end 215b) of the device 200.

In some embodiments, the helical wind of the first wire 220a extends only along a portion of the length of the device 200.

The helical wind of the first wire 220a forms a circuit such that, when desired, electric current 225 can be made to flow through the helical wind of the first wire 220a in a first direction and, when desired, in a second direction opposite to the first direction.

It should be appreciated that due to flowing current, the helical wind of the first wire 220a functions as an electromagnet or solenoid. Thus, when electric current 225 flows in the first direction, a magnetic force/field is generated having a first polarity. When electric current 225 flows in the second direction a magnetic force/field is generated having a second polarity opposite to the first polarity. Thus, the polarity of the generated magnetic field can be adjusted from the first polarity to the second polarity and vice versa by reversing the external wires that connect to the helical wind of the first wire 220a.

As shown, a second wire 220b is removably positioned within the lumen 205. In other words, the second wire 220b can be positioned within the lumen 205 and removed therefrom as and when required.

In some embodiments, the second wire 220b is oriented substantially parallel to the longitudinal axis 222 when positioned within the lumen 205. In some embodiments, the second wire 220b is substantially linear.

In some embodiments, the second wire 220b may be configured as a helical wind. In embodiments, the second wire 220b extends along at least a portion of a length of the device 200 substantially along the longitudinal axis 222.

In some embodiments, the second wire 220b extends along an entire length (from the proximal end 215a to the distal end 215b) of the device 200. In some embodiments, the second wire 220b extends only along a portion of the length of the device 200.

The second wire 220b also forms a circuit such that, when desired, electric current can be made to flow through the second wire 220b in a first direction and, when desired, in a second direction opposite to the first direction.

It should be appreciated that due to flowing current, the second wire 220b functions as an electromagnet or solenoid. Thus, when electric current flows in the first direction, a magnetic force/field is generated having a first polarity. When electric current flows in the second direction a magnetic force/field is generated having a second polarity opposite to the first polarity. Thus, the polarity of the generated magnetic field can be adjusted from the first polarity to the second polarity and vice versa by reversing the external wires that connect to the second wire 220b. Stated differently, two electromagnets are generated and positioned adjacent to one another by applying current to the helical wind of the first wire 220a and to the removable second wire 220b.

It should be appreciated that the electrical current may be controlled through an actuator integrated into a housing or handle attached, coupled, or in electrical communication with the catheter. The actuator may be a button, switch, slider, or other interface that, when manipulated, cause a controller, which may comprise at least one processor executing a plurality of programmatic instructions stored via memory, to generate and transmit the electrical current or terminate the electrical current.

To ease introduction and positioning of the device 200 within a blood vessel or anatomical structure, the device 200 should be in the first state—that is, collapsed or contracted.

To enable the device 200 to be in the first state, the second wire 220b is positioned within the lumen 205 (if not already positioned therein) and electric current is made to flow through the second wire 220b in a first direction to generate a magnetic field of a first polarity. Electric current is also made to flow through the helical wind of the first wire 220a albeit in a second direction (opposite to the first direction) to generate a magnetic field of a second polarity opposite to the first polarity. Consequently, the helical wind of the first wire 220a and the second wire 220b attract each other causing the wall 210 to be pulled inwards towards the lumen 205 thereby putting the device 200 in the first state.

It should be appreciated, that in some embodiments the device 200 may already be in the first state, by default, for ease of introduction and positioning of the device 200 within the blood vessel or anatomical structure.

Once the device 200 is positioned at a target location within the blood vessel or anatomical structure, electric current is made to flow in a first direction through the helical wind of the first wire 220a and the second wire 220b, which causes the helical wind of the first wire 220a and the second wire 220b to develop the same first polarities. Consequently, the helical wind of the first wire 220a and the second wire 220b repel each other and in doing so cause the conduit wall 210 to be in the second state—that is, expanded. Thus, the repelling the helical wind of the first wire 220a and the second wire 220b force the conduit open so that it takes the shape of an elongated tube, catheter or conduit. As the wall 210 expands the inner diameter of the lumen 205 and the outer diameter of the device 200 increases. The volume, as well as the inner and outer surface areas, of the device 200 increases. When the current is unidirectional the device 200 will remain patent and if the magnetic fields are of sufficient strength, the repelling forces of the device 200 will withstand collapse if negative pressure (aspiration) is applied to the lumen 205.

To ease removal of the device 200 from the target position and/or to trap material (thrombus or clot material, for example) within the lumen 205 there may be a need to forcibly place the device 200 in the first state (collapsed or contracted).

To achieve the first state, the direction of flow of electric current is reversed to be in a second direction (opposite to the first direction) in the helical wind of the first wire 220a (or the second wire 220b) while the direction of flow of electric current continues to remain in the first direction in the second wire 220b (or the helical wind of the first wire 220a). This reversal creates opposite attractive magnetic forces, due to a first polarity in the first wire 220a and an opposite second polarity in the second wire 220b (or due to a first polarity in the second wire 220b and an opposite first polarity in the first wire 220a), that in turn collapses or contracts the device 200 thereby putting it in the first state.

Stated differently, when a polar charge is generated in the conduit wall 210 due to the embedded helically wounded first wire 220a and a similar polar charge is generated in the second wire 220b positioned in the lumen 205, the two like charges repel one another and expand the device 200. The device 200 can either expand fully or partially depending upon the amount of current applied which adjusts the strength of the magnetic fields and the opposing forces. In some embodiments, it may be preferred to leave the second wire 220b in the lumen 205 since repelling magnetic charges will function to keep the conduit lumen open.

In various embodiments, the entire length of the device 200 or only portions thereof can be expanded/dilated or collapsed/contracted depending upon clinical needs and goals.

In various embodiments, the device 200 of the present specification has a longitudinal length ranging from a first length 45 cm to a second length 150 cm (or any set of numerical increments therein, such as 45 cm to 50 cm or 60 cm to 130 cm), an internal diameter of the lumen 205 ranging from a first diameter 2 F (0.67 mm) when collapsed to a second diameter 22 F (7.3 mm) when fully expanded (or any set of numerical increments therein, such as 3 F to 7 F or 5 F to 20 F), an outer diameter of the device 200 ranging from a third diameter 4 F (1.3 mm) to a fourth diameter 24 F (8 mm) when fully expanded (or any set of numerical increments therein, such as 5 F to 8 F or 7 F to 24 F), a thickness of the wall 210 ranging from a first thickness 0.33 mm to a second thickness 1 mm (or any set of numerical increments therein, such as 0.4 mm to 0.8 mm or 0.5 mm to 1 mm), a volume of the device 200 ranging from a first volume 0.0035 cm$^3$ to a second volume 5,194.2 cm$^3$ (or any set of numerical increments therein, such as 0.05 cm$^3$ to 4000 cm$^3$ or 1 cm$^3$ to 5000 cm$^3$), and an outer surface area of the device 200 ranging from a first area 94.7 cm$^2$ to a second area 3,440 cm$^2$ (or any set of numerical increments therein, such as 100 cm$^2$ to 3000 cm$^2$ or 144 cm$^2$ to 3400 cm$^2$).

In some embodiments, in the first state, the wall 110 has a first surface area, encloses a first volume, and has a first circumference and, in the second state, the wall 110 has a second surface area, equal to the first surface area, a second circumference that is greater than the first circumference, and a second volume that is greater than the first volume.

In some embodiments, the device 100 of the present specification has a longitudinal length ranging from less than 50 cm to greater than 100 cm. In some embodiments, the length ranges from less than 60 cm to greater than 140 cm.

In some embodiments, the device 100 of the present specification has an internal diameter of the lumen 105 ranging from less than 6 F when collapsed to greater than 16 F when fully expanded. In some embodiments, an internal diameter of the lumen 105 ranges from less than 4 F when collapsed to greater than 18 F when fully expanded. In some embodiments, an internal diameter of the lumen 105 ranges from less than 4 F when collapsed to greater than 6 F when fully expanded. In some embodiments, an internal diameter of the lumen 105 ranges from less than 3 F when collapsed to greater than 20 F when fully expanded.

In some embodiments, the device 100 of the present specification has an outer diameter of the lumen 105 ranging from less than 8 F when collapsed to greater than 18 F when fully expanded. In some embodiments, an outer diameter of the lumen 105 ranges from less than 10 F when collapsed to greater than 17 F when fully expanded. In some embodiments, an outer diameter of the lumen 105 ranges from less than 5 F when collapsed to greater than 22 F when fully expanded.

In some embodiments, the device 100 of the present specification has a thickness of the wall 110 ranging from less than 0.4 mm to greater than 0.9 mm. In some embodiments, a thickness of the wall 110 ranges from less than 0.35 mm to greater than 0.75 mm.

In some embodiments, the device 100 of the present specification has a volume of the lumen 105 ranging from less than 1 cm$^3$ when collapsed to greater than 2,500 cm$^3$ when fully expanded. In some embodiments, a volume of the lumen 105 ranges from less than 0.5 cm$^3$ when collapsed to greater than 3,500 cm$^3$ when fully expanded. In some embodiments, a volume of the lumen 105 ranges from less than 0.1 cm$^3$ when collapsed to greater than 5,000 cm$^3$ when fully expanded. In some embodiments, a volume of the lumen 105 ranges from less than 0.005 cm$^3$ when collapsed to greater than 4,000 cm$^3$ when fully expanded.

In some embodiments, the device 100 of the present specification has an outer surface area ranging from less than 100 cm$^2$ to greater than 3,000 cm$^2$. In some embodiments, an outer surface area of the device 100 ranges from less than 300 cm$^2$ to greater than 2,000 cm$^2$.

In various embodiments, the wall of the device 200 is fabricated using materials such as medical grade thermoplastics, but not limited to polyurethane, PEBAX and nylon.

Figure 4:
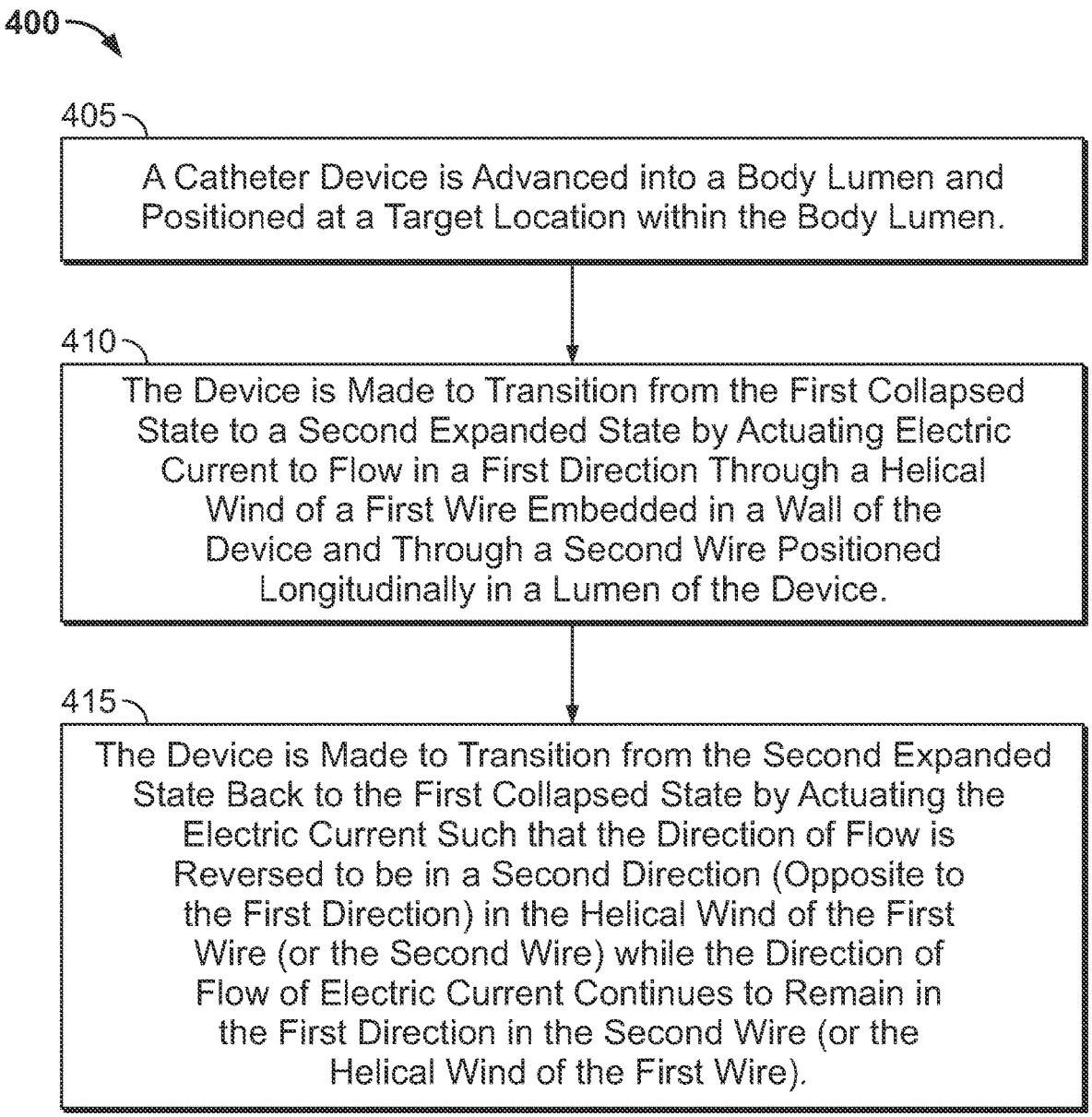
FIG. 4 is a flowchart of a plurality of steps of a method of using the device of FIG. 2, in accordance with some embodiments of the present specification.

FIG. 4 is a flowchart of a plurality of steps of a method 400 of using the manipulatable device 200 of FIG. 2, in accordance with some embodiments of the present specification.

In a non-limiting exemplary use case, the method 400 is implemented to use the device 200 to access a body lumen such as, for example, a lumen of a blood vessel or an anatomical structure for performing a mechanical aspiration thrombectomy.

At step 405, the device 200 is advanced into a body lumen and positioned at a target location within the body lumen.

In some embodiments, the device 200 is in a first state (that is, collapsed or contracted) during advancement and positioning at the target location.

In some embodiments, to enable positioning of the device 200 within the body lumen, a delivery catheter (having a detachable proximal hub, in some embodiments) is first advanced to the target location. Next, the proximal hub of the delivery catheter is removed and the device 200 is advanced (from a proximal end of the delivery catheter) through the delivery catheter to the target location.

In some embodiments, the device 200 has a detachable proximal hub and more proximally situated integrated aspiration and introducer side port. Thereafter, the proximal hub of the device 200 and the delivery catheter are removed thereby leaving the device 200 positioned at the target location.

At step 410, the device 200 is made to transition from the first state to a second state of being expanded or dilated. To enable this state transition, electric current is made to flow, using the actuator and controller, in a first direction through a helical wind of a first wire embedded in a wall of the device 200 and through a second wire positioned longitudinally in a lumen of the device 200. This causes the helical wind of the first wire and the second wire to develop the same first polarities. Consequently, the first wire and the second wire repel each other and cause the wall to be in the second state—that is, expand or dilate. Sustained application of the electric current holds the device 200 in an open position—that is, the second state. The device 200 can either expand fully or partially depending upon the amount of current applied which adjusts the strength of the magnetic fields and the resultant opposing forces.

At step 415, the device 200 is made to transition from the second state back to the first state. This may be needed to ease removal of the device 200 from the target position and/or to trap material (thrombus or clot material, for example) within the lumen of the device 200. To enable this state transition, the direction of flow of electric current is reversed to be in a second direction (opposite to the first direction) in the helical wind of the first wire (or the second wire) while the direction of flow of electric current continues to remain in the first direction in the second wire (or the helical wind of the first wire). This reversal creates opposite attractive magnetic forces that in turn collapses or contracts the device 200 thereby putting it back in the first state.

It should be appreciated, that step 405 assumes that the device 200 is in the first state by default.

In some embodiments, where the device 200 is not in the first state by default, the device 200 may need to be forced into the first state by ensuring that electric current flows in a first direction through the helical wind of the first wire (or the second wire) and flows in a second direction through the second wire (or the helical wind of the first wire) in order to create opposite polar charges causing them to be pulled towards each other (as also described in step 415).

Third Embodiment

FIG. 5 illustrates first and second views 502, 503 of a variable size lumen catheter or conduit device 500, in accordance with some embodiments of the present specification.

As shown in the first view 502, the device 500 has a circumferential wall 510 that encloses or surrounds (over an angular span of 360 degrees) a lumen 505. The device 500 also has proximal and distal ends 515a, 515b that are patent.

In embodiments, the conduit wall 510 is redundant (using foldable material and/or thin collapsible foils) such that the wall 510 can be transitioned from a first state to a second state and vice versa, as desired. In particular, when in a collapsed state, the conduit wall 510 comprises excess material such that it has a folded, rumpled, crimped, or crumbled configuration defining a first surface area and, when in an expanded state, the conduit wall 510 comprises a stretched or taut surface area having a second surface area, where the first and second surface areas are equal, even though the lumen of the conduit in the second state is greater than the lumen in the collapsed first state. The first state corresponds to a collapsed or contracted state of the wall 510 while the second state corresponds to an expanded or dilated state of the wall 510.

As shown in the transverse cross-sectional view 503, in some embodiments, a plurality of stacks of ferromagnets or magnets 520 is embedded within the wall 510 (that has a foldable material and/or thin collapsible foils between adjacent stacks 520) such that each of the plurality of stacks 520 is oriented substantially parallel to a longitudinal axis 522 of the device 500.

In embodiments, each of the plurality of stacks 520 further includes a plurality of ferromagnets.

In some embodiments, the plurality of stacks 520 are positioned longitudinally about the longitudinal axis 522 so that they cover an angular span of at least 1 degree and up to 360 degrees around the lumen 505.

In embodiments, the plurality of stacks 520 extends along at least a portion of the device 500 substantially parallel to the longitudinal axis 522. In some embodiments, the plurality of stacks 520 extends along the entire length (from the proximal end 515a to the distal end 515b) of the device 500.

In some embodiments, the plurality of stacks 520 extends only along a portion of the device 500.

In some embodiments, the plurality of stacks 520 includes at least two stacks positioned, preferably, diametrically opposite across the lumen 505.

In embodiments, each ferromagnet in each of the plurality of stacks 520 possesses a similar first magnetic polarity. Additionally, in a default state, the wall 510 (along with the embedded plurality of stacks 520) is restrained or fastened using a restraint (not shown) to keep the device 500 in the first state—that is, collapsed or contracted. According to the invention, the restraint can comprise at least one string, strap, mesh, cage, or chain wound around the outer surface of the wall 510 to restrain the wall 510 from expanding.

The device 500 further includes a first wire 521a having a plurality of ferromagnets strung, coupled or attached to the first wire 521a. Each of the plurality of ferromagnets of the first wire 521a possesses a similar second magnetic polarity opposite to the first polarity of the ferromagnets of the plurality of stacks 520. The first wire 521a can be removably positioned within the lumen 505 when desired.

The device 500 also includes a second wire 521b having a plurality of ferromagnets strung, coupled or attached to the second wire 521b. Each of the plurality of ferromagnets of the second wire 521b possesses a similar first magnetic polarity which is the same as the first polarity of the ferromagnets of the plurality of stacks 520. The second wire 521b can be removably positioned within the lumen 505 when desired.

When the restraint is removed, the magnets of the plurality of stacks 520 repel each other and the device 500 transitions to the second state (that is, expands or dilates) by opening the redundant or folded material of the wall 510. If desired, the second wire 521b may be advanced into the lumen 505 through the proximal end 515a to further force open the lumen 505 by using repellant magnetic forces between the ferromagnets of the second wire 521b and those of the plurality of stacks 520.

To transition the device 500 to the first state, the first wire 521a is introduced or advanced into the expanded lumen 505 from the proximal end 515a. Since the ferromagnets of the first wire 521a possess a polarity opposite to that of the plurality of stacks 520, introduction of the first wire 521a in the lumen generates an attractive magnetic force that pulls the wall 510 inwards and towards the lumen 505 thereby collapsing and transitioning the device 500 to the first state (that is, collapsed or contracted).

In various embodiments, the entire length of the device 500 or only portions thereof can be expanded/dilated or collapsed/contracted depending upon clinical need and goals.

In alternated embodiments, the magnets of the plurality of stacks 520 as well as the magnets of the first and second wires 521a, 521b are electromagnet cores.

In various embodiments, the device 500 of the present specification has a longitudinal length ranging from a first length 45 cm to a second length 150 cm (or any set of numerical increments therein, such as 45 cm to 50 cm or 60 cm to 130 cm), an internal diameter of the lumen 505 ranging from a first diameter 2 F (0.67 mm) when collapsed to a second diameter 22 F (7.3 mm) when fully expanded (or any set of numerical increments therein, such as 3 F to 7 F or 5 F to 20 F), an outer diameter of the device 500 ranging from a third diameter 4 F (1.3 mm) to a fourth diameter 24

F (8 mm) when fully expanded (or any set of numerical increments therein, such as 5 F to 8 F or 7 F to 24 F), a thickness of the wall 510 ranging from a first thickness 0.33 mm to a second thickness 1 mm (or any set of numerical increments therein, such as 0.4 mm to 0.8 mm or 0.5 mm to 1 mm), a volume of the device 500 ranging from a first volume 0.0035 cm$^3$ to a second volume 5,194.2 cm$^3$ (or any set of numerical increments therein, such as 0.05 cm$^3$ to 4000 cm$^3$ or 1 cm$^3$ to 5000 cm$^3$), and an outer surface area of the device 500 ranging from a first area 94.7 cm$^2$ to a second area 3,440 cm$^2$ (or any set of numerical increments therein, such as 100 cm$^2$ to 3000 cm$^2$ or 144 cm$^2$ to 3400 cm$^2$).

In some embodiments, in the first state, the wall 510 has a first surface area, encloses a first volume, and has a first circumference and, in the second state, the wall 510 has a second surface area, equal to the first surface area, a second circumference that is greater than the first circumference, and a second volume that is greater than the first volume.

In some embodiments, the device 500 of the present specification has a longitudinal length ranging from less than 50 cm to greater than 100 cm. In some embodiments, the length ranges from less than 60 cm to greater than 140 cm.

In some embodiments, the device 500 of the present specification has an internal diameter of the lumen 505 ranging from less than 6 F when collapsed to greater than 16 F when fully expanded. In some embodiments, an internal diameter of the lumen 505 ranges from less than 4 F when collapsed to greater than 18 F when fully expanded. In some embodiments, an internal diameter of the lumen 505 ranges from less than 4 F when collapsed to greater than 6 F when fully expanded. In some embodiments, an internal diameter of the lumen 505 ranges from less than 3 F when collapsed to greater than 20 F when fully expanded.

In some embodiments, the device 500 of the present specification has an outer diameter of the lumen 505 ranging from less than 8 F when collapsed to greater than 18 F when fully expanded. In some embodiments, an outer diameter of the lumen 505 ranges from less than 10 F when collapsed to greater than 17 F when fully expanded. In some embodiments, an outer diameter of the lumen 105 ranges from less than 5 F when collapsed to greater than 22 F when fully expanded.

In some embodiments, the device 500 of the present specification has a thickness of the wall 510 ranging from less than 0.4 mm to greater than 0.9 mm. In some embodiments, a thickness of the wall 510 ranges from less than 0.35 mm to greater than 0.75 mm.

In some embodiments, the device 500 of the present specification has a volume of the lumen 505 ranging from less than 1 cm$^3$ when collapsed to greater than 2,500 cm$^3$ when fully expanded. In some embodiments, a volume of the lumen 505 ranges from less than 0.5 cm$^3$ when collapsed to greater than 3,500 cm$^3$ when fully expanded. In some embodiments, a volume of the lumen 505 ranges from less than 0.1 cm$^3$ when collapsed to greater than 5,000 cm$^3$ when fully expanded. In some embodiments, a volume of the lumen 505 ranges from less than 0.005 cm$^3$ when collapsed to greater than 4,000 cm$^3$ when fully expanded.

In some embodiments, the device 500 of the present specification has an outer surface area ranging from less than 100 cm$^2$ to greater than 3,000 cm$^2$. In some embodiments, an outer surface area of the device 500 ranges from less than 300 cm$^2$ to greater than 2,000 cm$^2$.

In various embodiments, the wall 510 of the device 500 is fabricated using materials such as medical grade thermoplastics, but not limited to polyurethane, PEBAX and nylon.

FIG. 6 is a flowchart of a plurality of steps of a method 600 of using the magnetically manipulatable device 500 of FIG. 5, in accordance with some embodiments of the present specification.

In a non-limiting exemplary use case, the method 600 is implemented to use the device 500 to access a body lumen such as, for example, a lumen of a blood vessel or an anatomical structure for performing a mechanical aspiration thrombectomy.

As discussed earlier with reference to FIG. 5, the device 500 has a wall enclosing a lumen, a plurality of stacks of first magnets embedded within the wall, a first wire having a plurality of second magnets coupled thereto and a second wire having a plurality of third magnets coupled thereto, wherein the first and second wires are configured to be removably positioned within the lumen, wherein each magnet of the plurality of stacks has a first polarity, wherein each of the plurality of second magnets has a second polarity opposite to the first polarity, wherein each of the plurality of third magnets has the first polarity and wherein the device is kept in the first state using a restraint to restrain the wall.

At step 605, the device 500 is advanced into a body lumen and positioned at a target location within the body lumen.

In some embodiments, the device 500 is in a first state (that is, collapsed or contracted) during advancement and positioning at the target location.

In some embodiments, to enable positioning of the device 500 within the body lumen, a delivery catheter (having a detachable proximal hub, in some embodiments) is first advanced to the target location. Next, the proximal hub of the delivery catheter is removed and the device 500 is advanced (from a proximal end of the delivery catheter) through the delivery catheter to the target location.

In some embodiments, the device 500 has a detachable proximal hub and more proximally situated integrated aspiration and introducer side port. Thereafter, the proximal hub of the device 500 and the delivery catheter are removed thereby leaving the device 500 positioned at the target location.

At step 610, the device 500 is made to transition from the first state to a second state of being expanded or dilated. To enable this state transition, the restraint is removed and the device 500 assumes the second state. When the restraint is removed, the first magnets of the plurality of stacks repel each other causing the device 500 to assume the second state.

Optionally, while the device 500 is in the second state, the second wire is positioned within the lumen to force the lumen to open further.

At step 615, the device 500 is made to transition from the second state back to the first state. This may be needed to ease removal of the device 500 from the target position and/or to trap material (thrombus or clot material, for example) within the lumen of the device 500. To enable this state transition, the first wire is introduced and positioned within the lumen. When the first wire is positioned within the lumen an attractive magnetic force is generated between the first magnets of the plurality of stacks and the second magnets of the first wire causing the device 500 to be in the second state.

It should be appreciated that the catheter devices 100, 200 and 500 of the present specification can be used to access lumen of any anatomic structure in a body where an expandable catheter is desired. Also, the entire length of the devices 100, 200 and 500 or only portions thereof can be expanded/dilated or collapsed/contracted depending upon clinical need and goals.

Further, by collapsing the devices 100, 200 and 500, when needed, these can be used to capture material, traverse anatomy, and aid in retraction/removal. Still further, the devices 100, 200 and 500 do not need to have superior trackability because each will be delivered coaxially to its target through an already positioned larger bore catheter.

Fourth Embodiment

Figure 7:
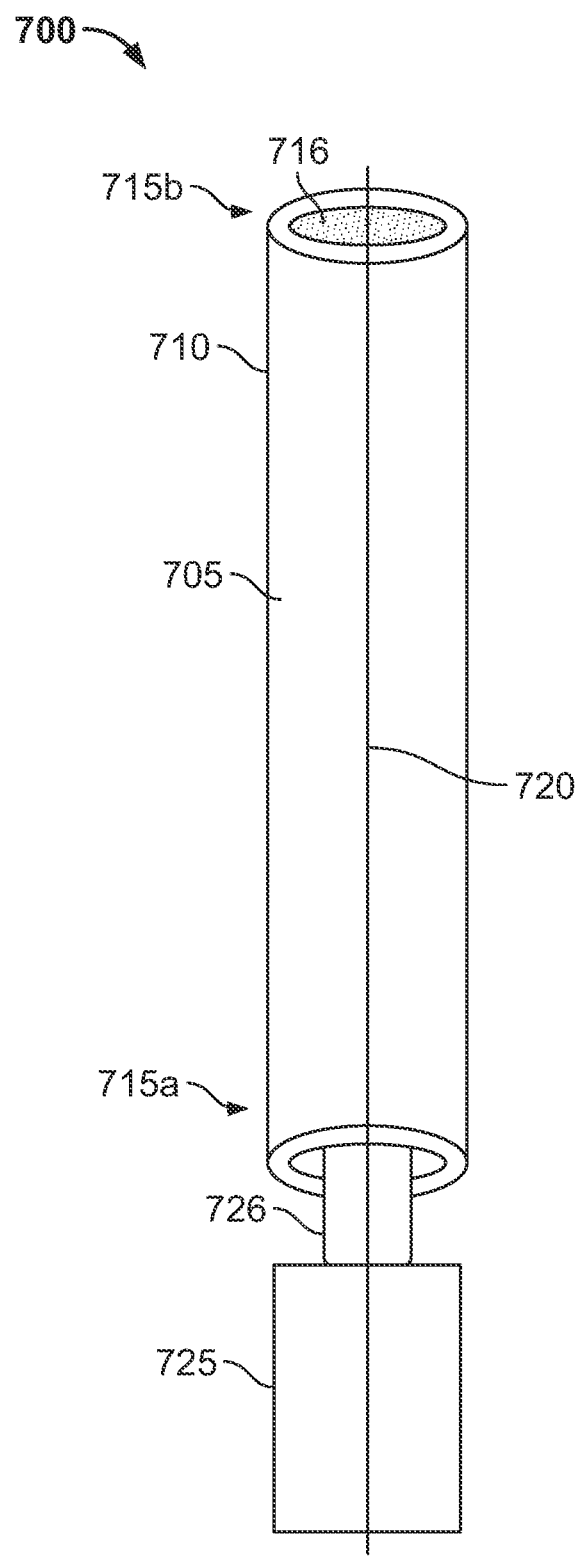
FIG. 7 illustrates another catheter or conduit device, in accordance with some embodiments of the present specification.

FIG. 7 illustrates a variable size lumen catheter or conduit device 700, in accordance with some embodiments of the present specification. The device 700 has a circumferential wall 710 that encloses or surrounds (over an angular span of 360 degrees) a lumen 705 extending from a proximal end 715a to a distal end 715b.

In embodiments, the wall 710 is redundant (using foldable material and/or thin collapsible foils) such that the wall 710 can be transitioned from a first state to a second state, when desired. The first state corresponds to a collapsed or contracted state of the wall 710 while the second state corresponds to an expanded or dilated state of the wall 710.

In particular, when in a collapsed state, the conduit wall 710 comprises excess material such that it has a folded, rumpled, crimped, or crumbled configuration defining a first surface area and, when in an expanded state, the conduit wall 710 comprises a stretched or taut surface area having a second surface area, where the first and second surface areas are equal, even though the lumen of the conduit in the second state is greater than the lumen in the collapsed first state.

In the first state, optionally, an aperture at the distal end 715b is occluded by a membrane 716 or a forced restriction 716 that blocks the aperture. The device 700 further includes a wire 720 that is removably positioned within the lumen 705, when the device 700 is in the first state. In the first state, the wire 720 extends through the collapsed lumen 705 to provide longitudinal rigidity while the device 700 is advanced through a previously inserted guide catheter and/or delivery catheter within a body lumen. When the device 700 is positioned proximate a target location within the body lumen, the wire 720 is removed from the lumen 705.

The device 700 also includes an indeflator 725 that is secured to the proximal end 715a via a luer lock 726. The indeflator 725 is an inflation or deflation device, such as a pump, that is configured to deliver a fluid, such as water or saline, and air via the luer lock 726 into the device 700.

The indeflator 725 is used to accurately pump fluid into the lumen 705 to enable the device 700 to transition from the first state to the second state (when the device 700 is positioned proximate a target location within the body lumen).

When the injected fluid pressure in the lumen 705 reaches a predefined critical pressure 'p' atm (1 atm=760 mm Hg=101,325 N/m2=760 torr) the distal membrane 716 optionally tears or the distal outflow restriction 716 optionally opens. The intra-conduit luminal pressure 'p' atm that develops prior to opening of the distal aperture is the mechanism that transitions the device 700 from the first state (that is, collapsed or contracted state) to the second state (that is, the expanded or dilated state).

Stated differently, the transition of the device 700, from the first state to the second state, is enabled by using the indeflator 725 to inject a fluid into the proximal end 715a of the lumen 705, wherein, when the injected fluid is injected into the lumen 705 and increases pressure within the lumen 705, the wall 710 of the device 700 expands from the first state to the second state and, when a pressure in the lumen 705 from the injected fluid reaches or exceeds a threshold pressure, the distal membrane, distal outflow restriction or occluded aperture 716 ruptures or opens to permit the fluid to flow out of the lumen 705 with the wall 710 remaining in the second state.

It should be appreciated that, while being in the second state as the device 700 is pulled back into the guide catheter and/or delivery catheter, the device 700 will transition from the second state to a partially collapsed state since the circumferential wall 710 will now take the shape and size of the guide catheter and/or delivery catheter.

In various embodiments, the device 700 of the present specification has a longitudinal length ranging from a first length 45 cm to a second length 150 cm (or any set of numerical increments therein, such as 45 cm to 50 cm or 60 cm to 130 cm), an internal diameter of the lumen 705 ranging from a first diameter 2 F (0.67 mm) when collapsed to a second diameter 22 F (7.3 mm) when fully expanded (or any set of numerical increments therein, such as 3 F to 7 F or 5 F to 20 F), an outer diameter of the device 700 ranging from a third diameter 4 F (1.3 mm) to a fourth diameter 24 F (8 mm) when fully expanded (or any set of numerical increments therein, such as 5 F to 8 F or 7 F to 24 F), a thickness of the wall 710 ranging from a first thickness 0.33 mm to a second thickness 1 mm (or any set of numerical increments therein, such as 0.4 mm to 0.8 mm or 0.5 mm to 1 mm), a volume of the device 700 ranging from a first volume 0.0035 cm$^3$ to a second volume 5,194.2 cm$^3$ (or any set of numerical increments therein, such as 0.05 cm$^3$ to 4000 cm$^3$ or 1 cm$^3$ to 5000 cm$^3$), and an outer surface area of the device 700 ranging from a first area 94.7 cm$^2$ to a second area 3,440 cm$^2$ (or any set of numerical increments therein, such as 100 cm$^2$ to 3000 cm$^2$ or 144 cm$^2$ to 3400 cm$^2$).

In some embodiments, in the first state, the wall 710 has a first surface area, encloses a first volume, and has a first circumference and, in the second state, the wall 710 has a second surface area, equal to the first surface area, a second circumference that is greater than the first circumference, and a second volume that is greater than the first volume.

In some embodiments, the device 700 of the present specification has a longitudinal length ranging from less than 50 cm to greater than 100 cm. In some embodiments, the length ranges from less than 60 cm to greater than 140 cm.

In some embodiments, the device 700 of the present specification has an internal diameter of the lumen 705 ranging from less than 6 F when collapsed to greater than 16 F when fully expanded. In some embodiments, an internal diameter of the lumen 705 ranges from less than 4 F when collapsed to greater than 18 F when fully expanded. In some embodiments, an internal diameter of the lumen 705 ranges from less than 4 F when collapsed to greater than 6 F when fully expanded. In some embodiments, an internal diameter of the lumen 705 ranges from less than 3 F when collapsed to greater than 20 F when fully expanded.

In some embodiments, the device 700 of the present specification has an outer diameter of the lumen 705 ranging from less than 8 F when collapsed to greater than 18 F when fully expanded. In some embodiments, an outer diameter of the lumen 705 ranges from less than 10 F when collapsed to greater than 17 F when fully expanded. In some embodiments, an outer diameter of the lumen 705 ranges from less than 5 F when collapsed to greater than 22 F when fully expanded.

In some embodiments, the device 700 of the present specification has a thickness of the wall 710 ranging from less than 0.4 mm to greater than 0.9 mm. In some embodiments, a thickness of the wall 710 ranges from less than 0.35 mm to greater than 0.75 mm.

In some embodiments, the device 700 of the present specification has a volume of the lumen 705 ranging from less than 1 cm$^3$ when collapsed to greater than 2,500 cm$^3$ when fully expanded. In some embodiments, a volume of the lumen 705 ranges from less than 0.5 cm$^3$ when collapsed to greater than 3,500 cm$^3$ when fully expanded. In some embodiments, a volume of the lumen 705 ranges from less than 0.1 cm$^3$ when collapsed to greater than 5,000 cm$^3$ when fully expanded. In some embodiments, a volume of the lumen 705 ranges from less than 0.005 cm$^3$ when collapsed to greater than 4,000 cm$^3$ when fully expanded.

In some embodiments, the device 700 of the present specification has an outer surface area ranging from less than 100 cm$^2$ to greater than 3,000 cm$^2$. In some embodiments, an outer surface area of the device 700 ranges from less than 300 cm$^2$ to greater than 2,000 cm$^2$.

In various embodiments, the wall 710 of the device 700 is fabricated using materials such as medical grade thermoplastics such as, but not limited to, polyurethane, PEBAX and nylon.

Figure 8:
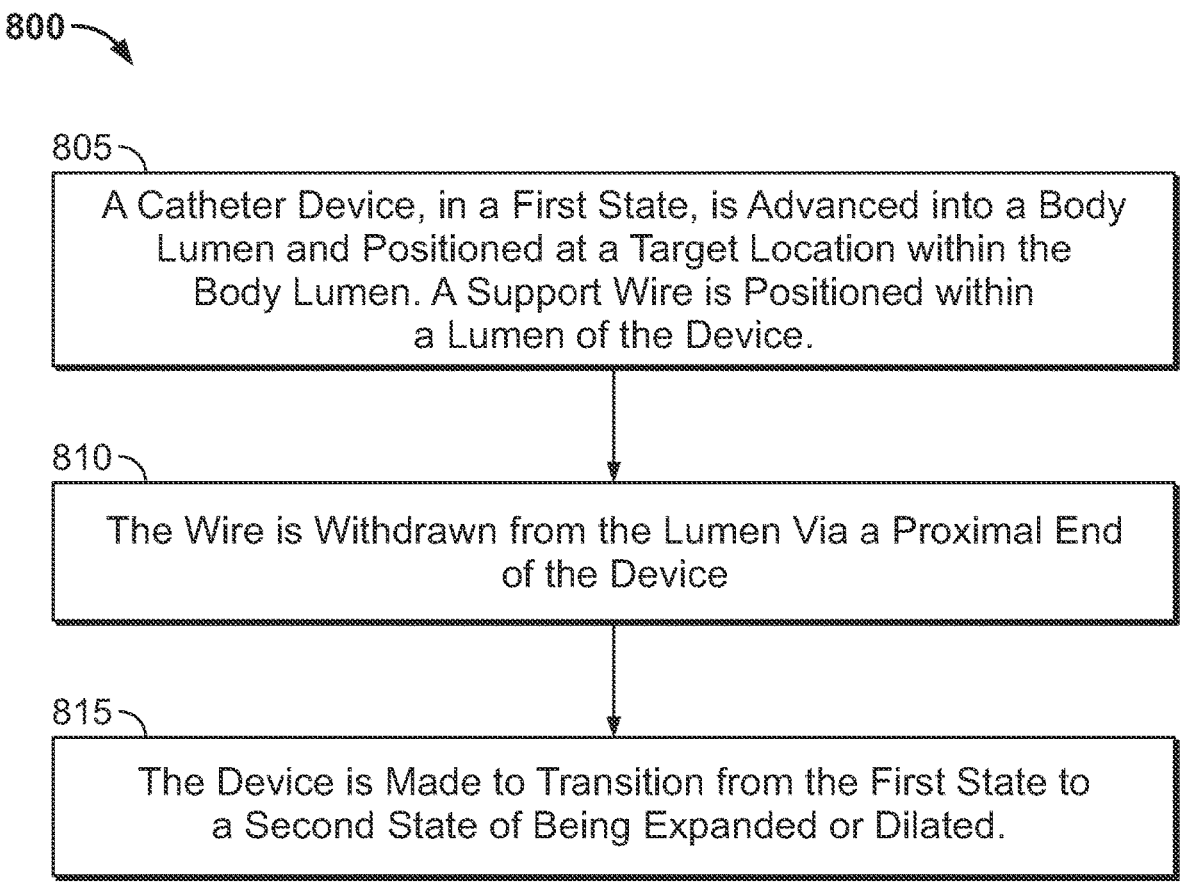
FIG. 8 is a flowchart of a plurality of steps of a method of using the catheter or conduit device of FIG. 7, in accordance with some embodiments of the present specification.

FIG. 8 is a flowchart of a plurality of steps of a method 800 of using the device 700 of FIG. 7, in accordance with some embodiments of the present specification.

In a non-limiting exemplary use case, the method 800 is implemented to use the device 700 to access a body lumen such as, for example, a lumen of a blood vessel or an anatomical structure for performing a mechanical aspiration thrombectomy.

At step 805, the device 700 is advanced into a body lumen and positioned at a target location within the body lumen.

In some embodiments, the device 700 is in a first state (that is, collapsed or contracted) during advancement and positioning at the target location. In the first state, an aperture at a distal end (distal aperture) of the device 700 is optionally occluded by a membrane or a forced restriction that blocks the distal aperture. A support wire is positioned within the lumen of the device 700.

In some embodiments, to enable positioning of the device 700 within the body lumen, a delivery catheter (having a detachable proximal hub, in some embodiments) is first advanced to the target location. Next, the proximal hub of the delivery catheter is removed and the device 700 is advanced (from a proximal end of the delivery catheter) through the delivery catheter to the target location. Thereafter, the delivery catheter may be removed thereby leaving the device 700 positioned at the target location.

At step 810, the wire is withdrawn from the lumen via a proximal end of the device 700.

Next, at step 815, the device 700 is made to transition from the first state to a second state of being expanded or dilated. To enable this state transition, an indeflator coupled to the proximal end of the device 700 is activated to inject fluid into the lumen until the fluid pressure within the lumen reaches or exceeds a predefined threshold pressure 'p'.

Optionally, when the fluid pressure reaches or exceeds the predefined threshold pressure 'p' the distal membrane tears, or the distal outflow restriction opens. The intra-conduit luminal pressure 'p' that develops prior to opening of the distal aperture transitions the device 700 from the first state to the second state.

Figure 9:
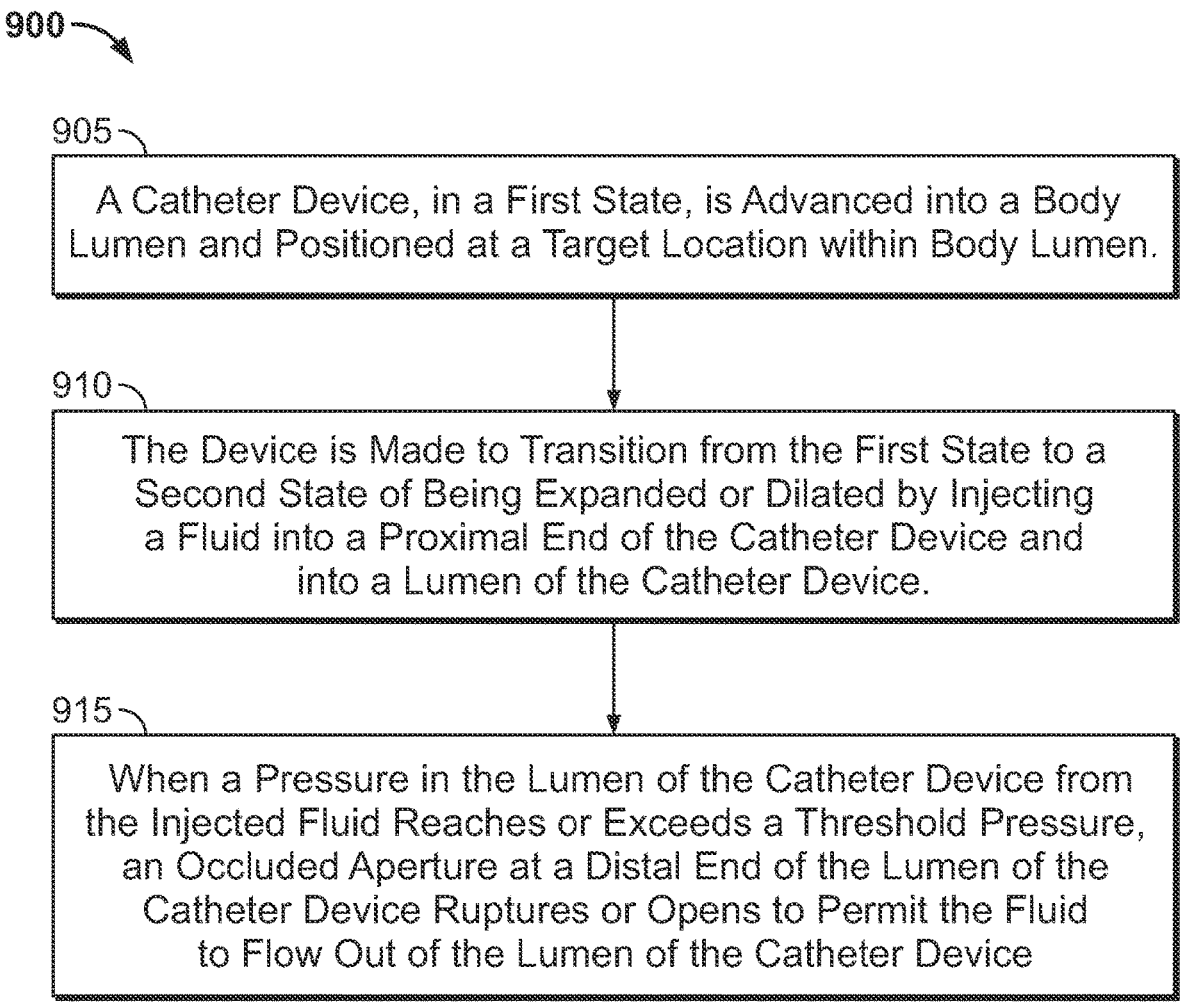
FIG. 9 is a flowchart of a plurality of steps of another method of using the catheter or conduit device of FIG. 7, in accordance with some embodiments of the present specification.

FIG. 9 is a flowchart of a plurality of steps of another method 900 of using the device 700 of FIG. 7, in accordance with some embodiments of the present specification. In a non-limiting exemplary use case, the method 900 is implemented to use the device 700 to access a body lumen such as, for example, a lumen of a blood vessel or an anatomical structure for performing a mechanical aspiration thrombectomy.

At step 905, the device 700 is advanced into a body lumen and positioned at a target location within the body lumen.

In some embodiments, the device 700 is in a first state (that is, collapsed or contracted) during advancement and positioning at the target location. In the first state, an aperture at a distal end (that is, a distal aperture) of the device 700 is optionally occluded by a membrane or a forced restriction that blocks the distal aperture.

Optionally, in some embodiments, a support wire is positioned within the lumen of the device 700.

In some embodiments, to enable positioning of the device 700 within the body lumen, a delivery catheter (having a detachable proximal hub, in some embodiments) is first advanced to the target location. Next, the proximal hub of the delivery catheter is removed and the device 700 is advanced (from a proximal end of the delivery catheter) through the delivery catheter to the target location. Thereafter, the delivery catheter may be removed thereby leaving the device 700 positioned at the target location.

Next, at step 910, the device 700 is made to transition from the first state to a second state of being expanded or dilated by injecting fluid into a proximal end of the device 700 and into a lumen of the device 700. To enable this state transition, an indeflator coupled to a proximal end of the device 700 is activated to inject fluid into the lumen till the fluid pressure within the lumen reaches or exceeds a predefined threshold pressure 'p'.

When the fluid pressure reaches or exceeds the predefined threshold pressure 'p' the distal membrane tears or the distal outflow restriction opens at step 915, permitting fluid to flow out of the lumen of the device 700. The intra-conduit luminal pressure 'p' that develops prior to opening of the distal aperture transitions the device 700 from the first state to the second state.

Stated differently, the state transition of the device 700 is enabled by using the indeflator to inject a fluid into the proximal end of the lumen, wherein, when the injected fluid is injected into the lumen and increases pressure within the lumen, the wall 710 of the device 700 expands from the first state to the second state and, when a pressure in the lumen from the injected fluid reaches or exceeds a threshold pressure, the distal membrane, distal outflow restriction or occluded aperture ruptures or opens to permit the fluid to flow out of the lumen with the wall remaining in the second state.

Optionally, in some embodiments, the support wire is withdrawn from the lumen via the proximal end of the device 700 prior to transitioning the device 700 from the first state to the second state.

The above examples are merely illustrative of the many applications of the catheter devices of present specification.

Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:
1. A catheter device, comprising:
 a conduit comprising a proximal end, a distal end and an outer wall, said conduit further comprising an internal lumen that extends from said proximal end of said conduit to said distal end of said conduit, said conduit adapted to transition from a pre-collapsed state to a first collapsed state, and from said first collapsed state to a second expanded state, said conduit further comprising a first plurality of electrical conduits and a second plurality of electrical conduits, each of said first and second plurality of electrical conduits embedded in said outer wall of said conduit, each of said first and second plurality of electrical conduits adapted to transmit electrical current therethrough in a first direction and an opposing second direction, said conduit further adapted to transition from said pre-collapsed state to said first collapsed state when said first plurality of electrical conduits transmits a first electrical current in said first direction and said second plurality of electrical conduits transmits a second electrical current in said second direction, and transition from said first collapsed state to said second expanded state when said first plurality of electrical conduits and said second plurality of electrical conduits transmit a third electrical current in said first direction.

2. The catheter device of claim 1, wherein said conduit further comprises a longitudinal axis disposed substantially parallel to said outer wall.

3. The catheter device of claim 2, wherein said first and second plurality of electrical conduits are oriented in said outer wall substantially parallel to said longitudinal axis.

4. The catheter device of claim 1, wherein said device further comprises a controller in electrical communication with said first and second plurality of electrical conduits.

5. The catheter device of claim 4, wherein said controller is adapted to generate and transmit said first, second and third electrical currents.

* * * * *